United States Patent
Akiba

(10) Patent No.: US 6,561,971 B1
(45) Date of Patent: May 13, 2003

(54) ENDOSCOPE WITH MAGNIFICATION CHANGE FUNCTION

(75) Inventor: Haruo Akiba, Omiya (JP)

(73) Assignee: Fuji Photo Optical Co., Ltd., Saitama (JP)

( * ) Notice: Subject to any disclaimer, the term of this patent is extended or adjusted under 35 U.S.C. 154(b) by 0 days.

(21) Appl. No.: 09/563,949

(22) Filed: May 2, 2000

(30) Foreign Application Priority Data

May 7, 1999 (JP) ............................................. 11-127625

(51) Int. Cl.[7] ............................................... A61B 1/045
(52) U.S. Cl. ........................................ 600/168; 600/131
(58) Field of Search ................................ 600/131, 168, 600/147; 396/86

(56) References Cited

U.S. PATENT DOCUMENTS 5,305,038 A * 4/1994 Mogamiya .................... 396/86
5,564,560 A * 10/1996 Minelli et al. ................ 200/5 R

FOREIGN PATENT DOCUMENTS

| JP | 1-297034 | * 11/1989 | ............ A61B/1/00 |
| JP | 5-265646 | * 10/1993 | ............ G06F/3/033 |
| JP | 06169889 | 6/1994 | |
| JP | 10-127568 | * 5/1998 | ............ A61B/1/00 |

* cited by examiner

Primary Examiner—John Mulcahy
(74) Attorney, Agent, or Firm—Snider & Assoiciates; Ronald R. Snider

(57) ABSTRACT

This endoscope includes a magnification change manipulative switch made easy to manipulate in relation to an angle manipulative knob. That is, in an endoscope manipulative section with an angle manipulative knob for bending a front end and a magnification change manipulative switch disposed, two switch bodies making up the above magnification change manipulative switch are arranged in a direction nearly perpendicular to a rotation axis of the angle manipulation knob and disposed nearly in contact with each other so as to be retained by a retaining member to which a rubber cover is attached in an airtight condition. On an outer surface of this rubber cover, a convex portion for identifying function is provided. According to this endoscope, movement of a thumb between the angle manipulation knob and the magnification change manipulative switch is smoothed and the above convex portion enables a magnification change, for example, to a near side or to the far side, to be manipulated.

3 Claims, 4 Drawing Sheets

ENDOSCOPE WITH MAGNIFICATION CHANGE FUNCTION

BACKGROUND OF THE INVENTION

1. Field of the Invention

The present invention relates to a switching structure or the like for operating magnification change function of driving a lens to make an observing distance variable in an endoscope.

2. Description of the Prior Art

In the endoscope, so thick a manipulative section as manually seizable is disposed at a base end side of an inserting part, while disposed at this manipulative section are an angle manipulative knob (rotational member) for bending a front end and manipulative switches such as an air/water feeding switch and a photographing switch. And, while holding the manipulative section, for example, by his left hand, a user is so arranged as to manipulate the above-described angle manipulative knob and various manipulative switches with his fingers.

Besides, it has recently been proposed to incorporate a magnification change mechanism for modifying an observation distance, for example, at an inserting front end and to drive a movable lens, constituent members of this magnification change mechanism, by means of a motor or the like. That is, this proposal lies in transmitting a rotation driving force of the above motor to the magnification change drive mechanism by using a linear transmission member, e.g., a multiple coil spring member and converting the rotary motion of the above motor into a linear motion here so as to oscillate a given movable lens back and forth, thereby actualizing a magnification change operation.

BRIEF SUMMARY OF THE INVENTION

Object of the Invention

Meanwhile, a magnification change manipulative switch of such magnification change mechanism as mentioned above also is to be disposed as well as other manipulative switches at the above manipulative section, but it comes into question how they are attached to this endoscope manipulative section. That is, a switching manipulation for this magnification change is often made in relation to manipulating the above angle manipulative knob. For example, the target portion to be observed is projected out while bending the front end of an endoscope by means of the angle manipulative knob and a manipulation for magnifying or reducing this observation portion is made. Thus, such an arrangement as permitting the magnification change switch to be easily manipulated, for example, with a thumb of a user during the reciprocating travelling of this thumb is demanded between the angle manipulative knob and the magnification change knob.

Incidentally, so far, a configuration of an electric switch disposed at the endoscope manipulative section has been present as shown in Japanese Patent Laid-Open No. 6-169889.

The present invention was achieved in consideration of the above problem and its object is to provide an endoscope with the magnification change switch easily magnifiable in relation to the angle manipulative knob.

SUMMARY OF THE INVENTION

To attain the above object, an endoscope according to the present invention comprises an angle manipulative knob disposed at the manipulative section thereof for bending a front end and a magnification change manipulative switch disposed at a manipulative section of the endoscope for putting a magnification change drive unit into motion, wherein the above magnification change switch is made up of two switch bodies having individual switching functions, arranged in a direction nearly perpendicular to a rotation axis of the above angle manipulative knob and disposed nearly in contact with each other. Incidentally, the above magnification change switch can control the motion of a magnification change mechanism such as varifocal optical system for changing the observing distance or zooming optical system for making its focal length variable correspondingly.

According to the above configuration, two switching bodies are arranged in a direction nearly perpendicular to the rotation axis of the angle manipulative knob, i.e., in parallel to the rotational direction of the angle manipulative knob, and the distances of both pressing portions of these switching bodies from the angle manipulative knob become almost equal, so that a thumb of the hand holding the manipulative section is facilitated to move between the angle manipulative knob and the both pressing portions of the magnification change switch and these manipulations, (that of the angle manipulative knob conclusive), by using a thumb are smoothed.

With respect to the above magnification change switches, another invention can be configured by having the above two switch bodies retained by a single retaining member and attaching a rubber cover member to the above retaining member on which an identifiable ruggedness capable of identifying two functional operations is formed. According to this, two switch bodies are recognized as a single manipulation by means of a rubber cover member and two magnification change manipulations in a magnifying direction and in a reducing direction (direction for changing the focal length into the near or far side) can be smoothly performed on the basis of this identifiable ruggedness of the rubber cover member. Incidentally, instead of the configuration of claim 2, a rubber cover may be provided each of the above two switch bodies.

Two switch bodies of the above magnification change manipulation may comprise a switch body for manipulating the focal length toward a far direction and a switch body for manipulating the focal length toward a far direction.

Besides, with respect to the above magnification change switches, still other invention has the above switch bodies each comprising a double-step switch, in which a magnification change operation in a specified direction and the speed thereof are controlled by manipulating this individual double-step switch.

According to this other invention, both manipulating the magnification function (focal length) in near and far directions and manipulating the magnification changing speed becomes executable at one and the same manipulating position.

DETAILED DESCRIPTION OF THE PREFERRED EMBODIMENTS

Figure 1:
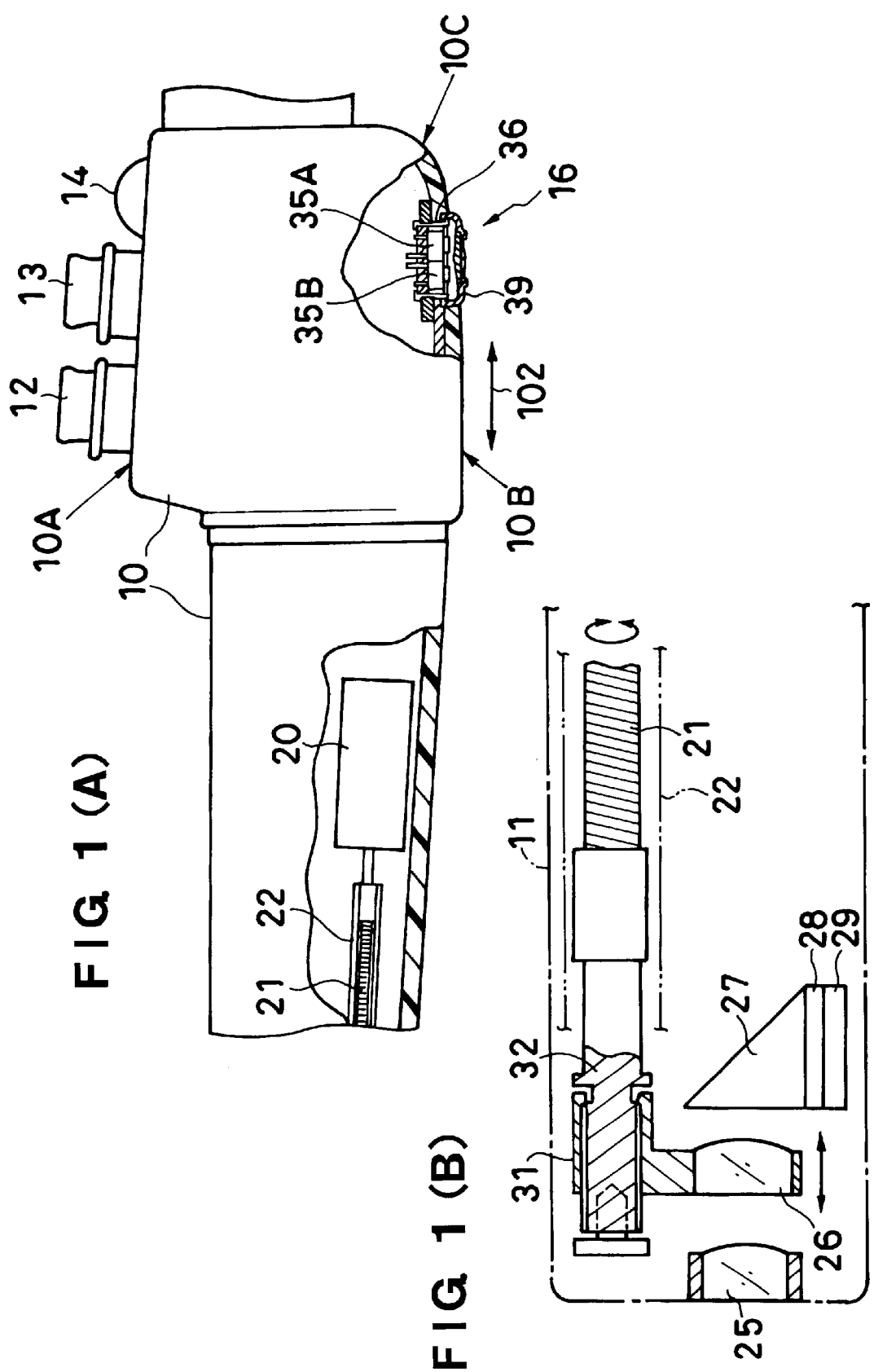
FIG. 1(A) is a configurational drawing of a manipulative section of an endoscope of magnification change function according to Embodiment 1 of the present invention and its neighborhood.
FIG. 1(B) is a configurational drawing of the front end side of an endoscope according to Embodiment 1 of the present invention.
Figure 2:
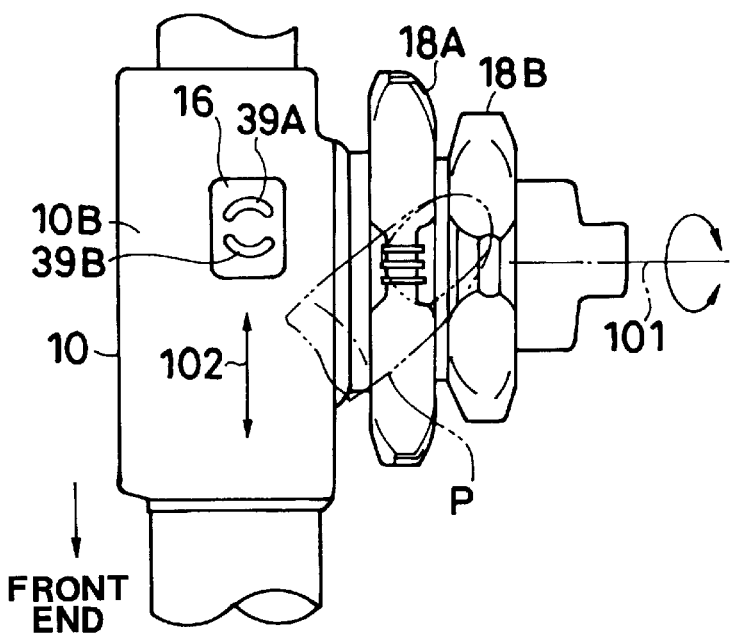
FIG. 2 is a bottom plan view of the endoscope manipulative section standing vertically in FIG. 1.
Figure 3:
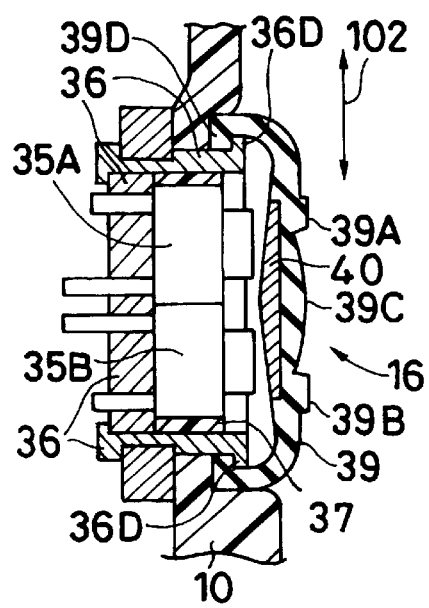
FIG. 3(A) is a sectional view showing the configuration of a magnification change switch according to Embodiment 1.
FIG. 3(B) is a front view of the switch of FIG. 3(A) when the rubber cover is removed.
FIG. 3(C) is a front view of the switch of FIG. 3(A) when the rubber cover is mounted.
Figure 3:
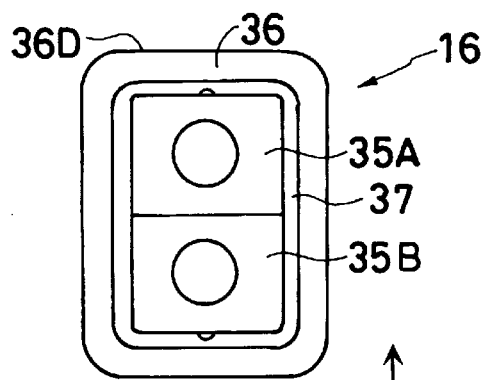
Figure 3:
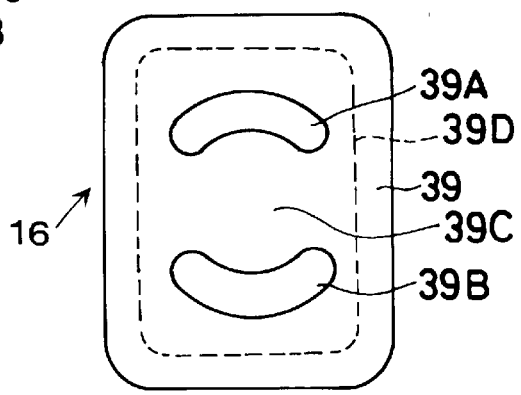

FIGS. 1 to 3 show the configuration of an endoscope with magnification change function according to Embodiment 1. First, the overall configuration of an endoscope will be described referring to FIGS. 1(A) and (B) and FIG. 2. FIG. 1(A) corresponds to an endoscope manipulative section 10, to the left of which the inserting part including the front end 11 of FIG. 1(B) is disposed, and is connected to a light source or processor unit via an unillustrated cable. At the rear of this manipulative section 10, an air/water feed button 12, a suction button 13 and a freezing switch 14 are provided and various switches such as VTR switch are disposed as well. And, to the disposed side 10B opposed to that 10A of the above air/water feed button 12 in this manipulative section 10, a magnification change switch 16 is attached which will be described below.

FIG. 2 is a drawing of the above manipulative section 10 settled vertically of FIG. 1 as viewed from the bottom of FIG. 1, on one side of which (at the rear of the manipulative section 10 of FIG. 1) a vertical angle knob 18A and a horizontal angle knob 18B are provided in such a manner as to rotate around the rotation axis 101. And, by rotationally manipulating this vertical angle knob 18A, the front end 11 can be bent vertically (up and down) via an internal wire, whereas the front end 11 can be bent horizontally (right and left) by using the horizontal angle knob 18B.

In FIG. 1(A), a magnification change driving unit 20 comprising a drive motor, a speed change gear or the like is disposed inside the manipulative section 10 to which a linear transmission member 21 comprising a multicoil spring or the like is connected. This linear transmission member 21 is led through a soft protective tube 22.

As shown in FIG. 1(B), an objective lens 25, a movable lens 26 for executing a magnification change and a prism 27 are disposed at the front end 11 and a CCD 29 serving for a solid pickup element is optically connected to this prism 27 via a cover glass 28. A retaining member 31 of the above described movable lens 26 has a female screw portion on its top, a rotation driving body 32 for screwing a male screw into the female screw is disposed at this female screw portion and the above linear transmission member 21 is linked to this rotation driving body 32.

Accordingly, on rotationally driving this linear transmission member 21 by means of the driving unit 20, the movable lens 26 moves back and forth by the screwed connection of the rotational drive body 32 and the retaining member 31, so that the observing distance (focal length) can be set to a far or near direction by the movement to the front or rear side. In this case, a varifocal optical system is used but other magnitude change drive mechanisms such as not varifocal zoom optical system may be used.

FIG. 3(A) to (C) show a detailed configuration of the above magnification change manipulative switch 16 and this magnification change manipulative switch 16 is configured by attaching two independent switch bodies 35A and 35B comprising, for example, tact switches or the like to the retaining member 36 via a packing 37 or the like. And, as apparent from FIG. 2, these switch bodies 35A and 35B are arranged along a direction 102 perpendicular to that of the rotation axis 101 of the above vertical angle knob 18A and horizontal angle knob 18B.

That is, as shown in FIG. 2, the magnification change switch 16 is provided in length along the rotational direction of the angle knobs 18 (A and B) and moreover is disposed a little above the extension position of the rotation axis 101 near the side of the angle knob 18 (rear end side of the endoscope) in view of the disposed side 10B. When a thumb P on the angle knob 18 is moved to the body side of the manipulative section 10, such a positional configuration allows this thumb P to be located on the magnification change switch 16 in a natural manner.

Besides, attached to the above retaining material 36 is a robber cover 39 covering the top of the two switch bodies 35A and 35B and serving as the manipulative plane, as shown in FIG. 3(A) to (C). That is, by mating a nail-shaped portion 39D on the bottom periphery of the rubber cover 39 to a collar-shaped portion 36D on the top periphery of the retaining member 36, the relevant rubber cover 39 is disposed with an airtight (waterproof) structure ensured.

In this rubber cover 39, not only a metal sheet 40 for facilitating one to press the switch bodies 35A and 35B is stuck to its inner side, but an arc-shaped (identifying) convex portion 39A indicating the manipulating position of the manipulative function region in a near (magnifying) direction and a convex portion 39B indicating the manipulative position of the manipulative function region in a far (reducing) direction are integrally formed also and consequently the central portion 39C of this rubber cover 39 is so formed in a heaped shape so as to distinguish the central portion. Thus, accordingly to this rubber cover 39, switch manipulations of two functions becomes performable while touching the shape of the convex portions 39A and 39B and the central portion 39C. Incidentally, since it can be considered to strongly press the above central portion 39C in error and also to simultaneously press both switch bodies 35A and 35B, a process of making the signal ineffective is so arranged as to be performed when both of the switch bodies 35A and 35B were pressed.

Embodiment 1 is configured as mentioned above, the magnification change manipulative switch 16 is disposed near the angle switches 18 (A and B) and the switch bodies 35A and 35B inside this switch 16 are arranged along a direction 102 perpendicular to that of the angle knob rotation axis 101, thereby enabling the thumb P of the hand holding the manipulative section 10 to smoothly move between the angle knobs 18 (A and B) and the magnification change manipulative switch 16.

Furthermore, there are advantages that the magnification change manipulation in a near direction and a far direction can be easily performed by a slight movement of the thumb P, such as i.e., by pressing the convex portion 39A with the finger tip and the convex portion 39B with the finger pad because the convex portion 39A and the convex portion 39B of the rubber cover 39 at the manipulative positions are adjacent to each other and moreover a manipulating direction (near or far direction) of the manipulative operation is easy to grasp because the finger moving direction between both of the convex portions 39A and 39B coincides with the rotation manipulating direction of the angle knobs 18 (A and B).

And, at the time of manipulating the above magnification change manipulative switch 16, the rotational drive force of the driving unit 20 of FIG. 1 is transmitted to the side of the front end 11 via the linear transmission member 21 and the movable lens 26 is moved back and forth by the rotational drive body 32, thereby enabling the image pickup magnification to be changed. Briefly, pressing the convex portion 39A of a rubber cover results in the movement of the focal length to a far direction and pressing the convex portion 39B of a rubber cover results in the movement of the focal length to a near direction.

Figure 4:
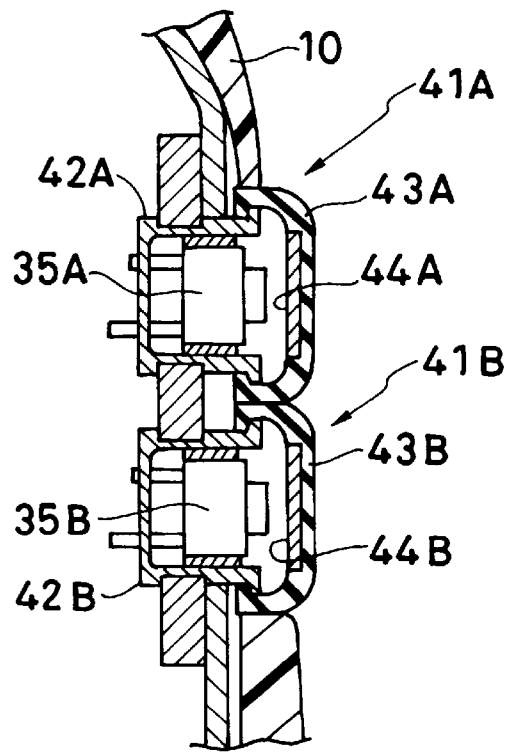
FIG. 4 is a sectional view showing the configuration of a magnification change switch according to Embodiment 2.
Figure 5:
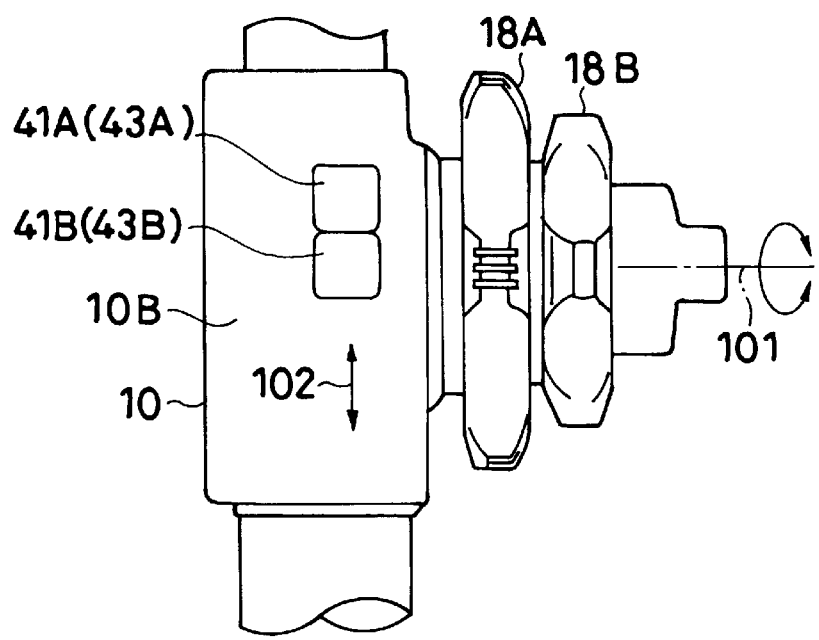
FIG. 5 is a side view of the endoscope manipulative section standing vertically according to Embodiment 2 viewed from the magnification change switch disposed side.

FIGS. 4 and 5 shows the configuration of Embodiment 2. This Embodiment 2 relates to a magnification change manipulative switch with rubber covers also separately provided. As shown in FIG. 4, a switch body 35A similar to that of Embodiment 1 is attached to a retaining member 42A and a rubber cover 43A is attached to this retaining member 42A in the upper magnification change manipulative switch 41A, whereas a switch body 35B is retained by a retaining member 42B and a rubber cover 43B is attached to this retaining member 42B also in the lower magnification change manipulative switch 41B. Attaching these rubber covers 43A and 43B to the retaining members 42A and 42B is performed by mating a nail-shaped portion to a collar-shaped portion as with Embodiment 1 so as to form an airtight condition (waterproof structure).

Besides, stuck to the inner side of the above rubber covers 43A and 43B are metal sheets 44A and 44B for facilitating one to press the switch bodies 35A and 35B. And, as shown in FIG. 5, two magnification change switches 41A and 41B (switch bodies 35A and 35B) end in being arranged along a direction 102 perpendicular to the rotation axis 101 of the angle knobs 18 (A and B) at positions similar to those of Embodiment 1.

According to Embodiment 2 also, a thumb can be moved naturally and smoothly between the angle knobs 18 (A and B) and the magnification change switches 41A and 41B while holding the manipulative section 10 and manipulating the magnification change switches 41A and 41B is also facilitated.

Figure 6:
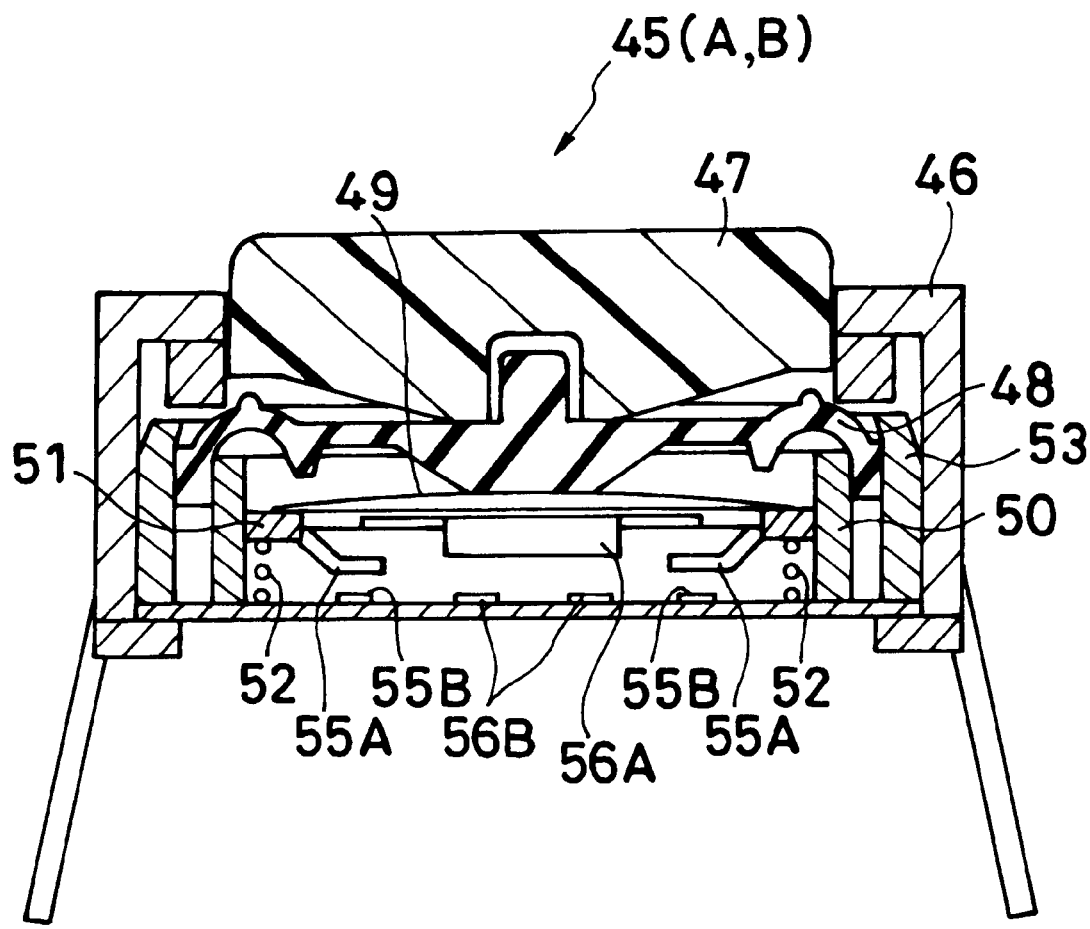
FIG. 6 is a sectional view showing the configuration of a double-step magnification change switch according to Embodiment 3.

FIG. 6 shows the configuration of a double-step switch according to Embodiment 3 usable in place of the above magnification change switches 16 and 41 (A and B) and not only the direction but the speed of a magnification change can be manipulated using this. In FIG. 6, a pressing portion 47 is disposed with vertical freedom at the opening of the retaining member 46 in the double-step switch 45 and an elastic movable contact 49 is disposed via a rubber cover 48 under this pressing portion 47. This movable contact 49 is attached to a movable plate 51 vertically moving in a support port 50 and this movable plate 51 is urged to the upper side by a spring 52. Incidentally, the above rubber cover 48 is so shaped as to put a lid on the upper surface of the above support portion 50 and the airtight (waterproof) structure inside the switch member is kept by pressing its peripheral side with a caulking member 53.

Besides, below this movable plate 51 is disposed a first-step terminal 55A and a second-step terminal 56A is attached to the above movable contact 49, whereas another first-step terminal 55B which the above terminal 55A is to contact and another second-step terminal 56B which the above terminal 56A is to contact are disposed on the lower base plate. Thus, contact between the first-step terminals 55A and 55B caused by pressing the above pressing portion 47 turns on the first-step switch and contact between the second-step terminals 56A and 56B caused by further pressing the pressing portion 47 turns on the second-step switch. Incidentally, on releasing the pressure on the above pressing portion 47, the movable contact 49 is restored to the upper side by its elasticity and the movable plate 51 returns to the initial position by a spring 52.

Two of such double-step switches 45 according to Embodiment 3 are disposed in place of the magnification change switches 41A and 41B in FIG. 4. According to one double-step magnification change switch 15A, the first-step pressing manipulation causes a magnification change operation into a near direction and the second-step pressing manipulation can increase the magnification changing speed into a near direction from a given value (e.g., a value of speed corresponding to the pressed duration is set up). On the other hand, according to another double-step magnification change switch 45B, a first-step pressing manipulation causes a magnification change operation into a far direction and a second-step pressing manipulation can increase the magnification changing speed into a far direction.

Incidentally, a configuration similar to that of a double-step magnification change switch 45 according to Embodiment 3 can be also used in place of a magnification change manipulative switch 16 according to Embodiment 1 and in this case, two switch portions each basically comprising a double-step switch according to Embodiment 3 are retained by one retaining member, this retaining member is to be covered with a single rubber cover as with Embodiment 1.

With the above embodiments, magnification change manipulative switches 16, 41 and 45 are respectively provided at the lateral side 10B of the manipulative section 10 as shown in individual figures, but may be provided elsewhere. In FIG. 1, for example, the corner 10C of the manipulative section 10 is made into a slant cut shape rather than the condition of FIG. 1 and the above magnification change manipulative switches 16, 41 and 45 maybe positioned at this slant position.

Further, although as a magnification change during mechanism, the configuration of the driving section 20 and the linear transmission member 21 arranged on the manipulation section 10 is applied, the magnification change driving mechanism in which other actuator is arranged on the end portion or the like.

As described above, according to Embodiments 1 to 3, magnification change manipulative switches become easy to manipulate in relation to angle manipulative knobs. Besides, by attaching a single rubber cover member with the function identifying ruggedness to one retaining member, the manipulative switches can be treated as a single body while the presence of two switch bodies left unconscious of and can be made easy to handle. Furthermore, provision of a double-step switch confers an advantage that both the manipulation of setting the focal length to a far or near direction and that of its change speed are executable by a pressing operation at one and the same position.

What is claimed is:

1. An endoscope with magnification change function comprising:
   an angle manipulative knob disposed at the manipulative section thereof for bending a front end;
   a magnification change manipulative switch disposed at a manipulative section of the endoscope for operating a magnification change driving unit, wherein said magnification change manipulative switch is made up of two switch bodies, having individual switching functions, arranged in a direction nearly perpendicular to a rotation axis of said angle manipulative knob and disposed nearly in contact with each other;

wherein said magnification change manipulative switch comprises a rubber cover portion with ruggedness capable of identifying two functional manipulations; and wherein operation of magnification change manipulative switch is by movement of a thumb; and wherein said magnification change manipulative switch has said switch bodies each consisting of a double-step switch and both magnification change operation in a specified direction and a speed of the magnification change operation are controlled by manipulating this individual double-step switch.

2. An endoscope with magnification change function comprising:

an angle manipulative knob disposed at the manipulative section thereof for bending a front end;

a magnification change manipulative switch disposed at a manipulative section of the endoscope for operating a magnification change driving unit, wherein said magnification change manipulative switch is made up of two switch bodies, having individual switching functions, arranged in a direction nearly perpendicular to a rotation axis of said angle manipulative knob and disposed nearly in contact with each other;

wherein said magnification change manipulative switch comprises a rubber cover portion with ruggedness capable of identifying two functional manipulations;

wherein operation of magnification change manipulative switch is by movement of a thumb;

wherein said magnification change manipulative switch comprises a single retaining member retaining said two switch bodies, and a single rubber cover portion covering the top of said two switch bodies and having ruggedness of a different shape capable of identifying two functional manipulations; and wherein said rubber cover portion comprises, a metal sheet which is provided on a reverse of the rubber cover and the metal sheet also has a surface which is diagonally cut which provides for a high central part for facilitating pushing two switches.

3. An endoscope with magnification change function comprising:

an angle manipulative knob disposed at the manipulative section thereof for bending a front end;

a magnification change manipulative switch disposed at a manipulative section of the endoscope for operating a magnification change driving unit, wherein said magnification change manipulative switch is made up of two switch bodies, having individual switching functions, arranged in a direction nearly perpendicular to a rotation axis of said angle manipulative knob and disposed nearly in contact with each other;

wherein said magnification change manipulative switch comprises a rubber cover portion with ruggedness capable of identifying two functional manipulations; and wherein said magnification change manipulative switch has said switch, bodies each consisting of a double-step switch and both magnification change operation in a specified direction and a speed of the magnification change operation are controlled by manipulating this individual double-step switch.

* * * * *